United States Patent [19]

Wojciechowicz, Jr.

[11] Patent Number: 4,932,952
[45] Date of Patent: Jun. 12, 1990

[54] ANTISHOCK, ANTICLOG SUCTION COAGULATOR

[75] Inventor: Alex F. Wojciechowicz, Jr., Princeton, N.J.

[73] Assignee: Alto Development Corporation, Farmingdale, N.J.

[21] Appl. No.: 287,386

[22] Filed: Dec. 20, 1988

[51] Int. Cl.⁵ .......................................... A61B 17/36
[52] U.S. Cl. ............................................................ 606/49
[58] Field of Search ............ 128/303.1, 303.13–303.17; 606/41, 49–52

[56] References Cited

U.S. PATENT DOCUMENTS

| | | | |
|---|---|---|---|
| 2,888,928 | 6/1959 | Seiger | 128/303.17 |
| 3,595,234 | 7/1971 | Jackson | 604/119 |
| 3,610,242 | 10/1971 | Sheridan et al. | 128/766 |
| 3,828,780 | 8/1974 | Morrison, Jr. | 128/303.17 |
| 3,875,945 | 4/1975 | Friedman | 128/303.14 |
| 3,974,833 | 8/1976 | Durden | 128/303.17 |
| 4,427,006 | 1/1984 | Nottke | 128/303.17 |
| 4,562,838 | 1/1986 | Walker | 128/303.17 |
| 4,719,914 | 1/1988 | Johnson | 128/303.17 |

*Primary Examiner*—Max Hindenburg
*Attorney, Agent, or Firm*—Mathews, Woodbridge & Collins

[57] ABSTRACT

A suction coagulator includes an improved venting system and suction tip to minimize the potential of electrical shock hazard for the surgeon using the apparatus. The nonconductive, plastic handle of the device is attached to the proximal end of an insulated, conductive metal cannula at the distal end of which is located the cauterizing, suction tip. A suction fitting at the rear end of the handle communicates through the hollow interior cavity of the handle and the interior channel in the cannula with the cauterizing tip. A suction control finger operated venting port located on the exterior of the handle is connected by a passageway to the interior cavity. It has been found that the tendency of the suction control passageway to fill up with blood significantly decreases if at least a portion of the suction control venting port is located downstream of the proximal end of the cannula. The cauterizing tip of the cannula includes a primary suction port at its very end and at least one secondary suction port located in the sidewall of the cannula and approximately 1–5 mm away from the primary suction port. The secondary suction port significantly assists in preventing the cauterizing tip from becoming clogged with tissue and blood. The improved structure significantly decreases the shock hazard to the surgeon and increases the utility of the device.

15 Claims, 2 Drawing Sheets

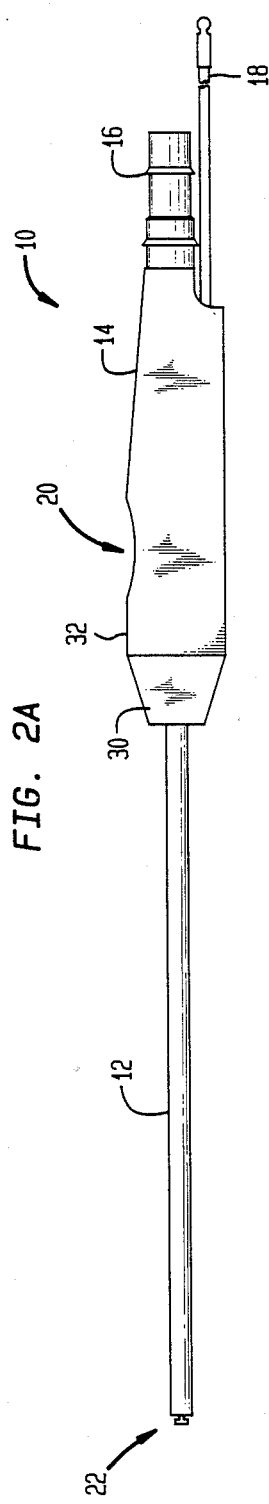
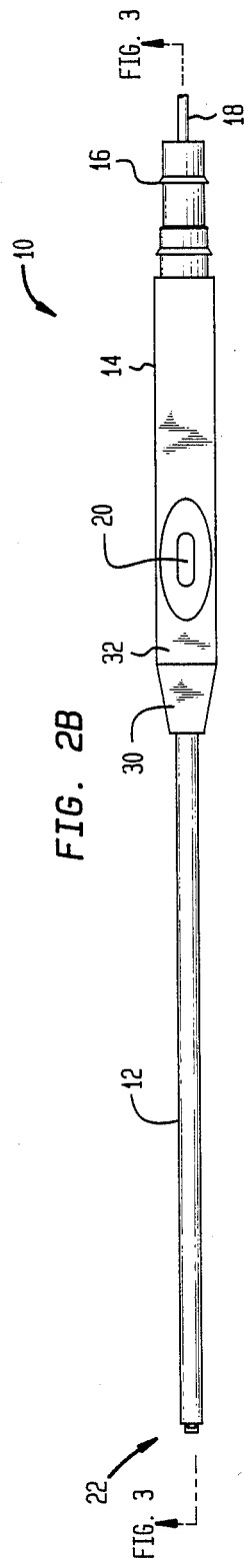
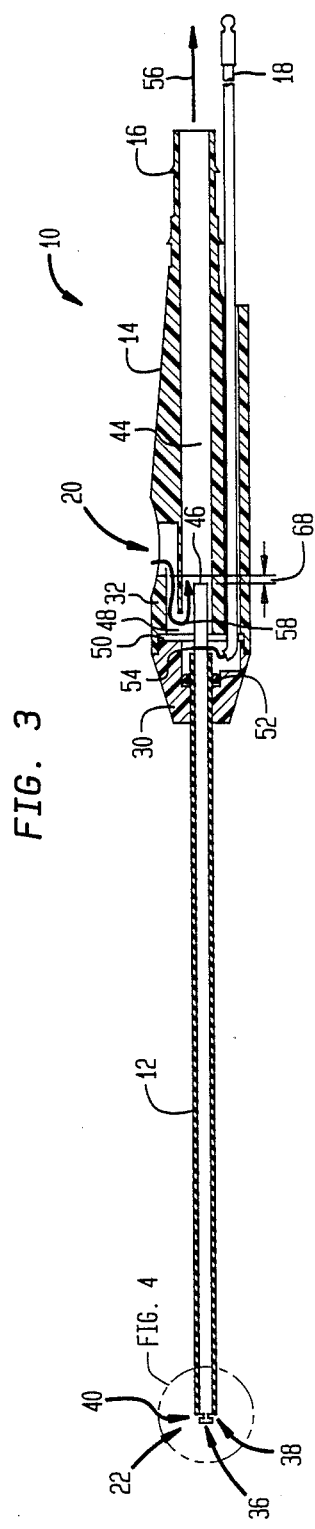

ANTISHOCK, ANTICLOG SUCTION COAGULATOR

BACKGROUND OF THE INVENTION

1. Field of the Invention

The invention relates to a suction electrocoagulator apparatus having an anticlogging tip and a suction control, finger operated venting port located at least partially downstream of the proximal end of the conductive cannula.

2. Description of Related Art

The coagulation of bleeding blood vessels using electrically conductive suction tubes also referred to as cannulas is a technique widely used for over two decades. A combined electrocautery and suction tube instrument is employed in surgery wherever excessive blood must be removed from the bleeding site in order to facilitate hemostat of bleeding vessels using the electrocautery feature of the instrument.

Commercially available suction coagulators made expressly for electrocautery hemostat procedures typically have the following common components:

(A) A hollow metallic tube having a suitable thickness of nonconducting electrical insulation on its exterior. The electrical insulation is absent from the last few millimeters on the tube's distal end in order to form an annular ring for electrocautery procedures. The sole purpose of the electrical insulation is to protect the patient and doctor from cautery burns that would result from contact with the outside of the metallic tube when it is energized.

(B) A non-metallic or electrically insulated handle. The handle includes a suction cavity or passageway running through its length that terminates in a suction fitting at one end for connection to a suction source. At its proximal end the handle is hermetically coupled to the hollow metallic tube so that the suction cavity of the handle communicates directly with the suction channel of the tube. The handle also may have a venting passageway that connects the main suction cavity with a vent hole on the handle's exterior. The surgeon uses finger pressure on the vent hole to control the amount of suction applied.

(C) A power cord, typically an insulated wire, is used to connect the suction coagulator to a high frequency current generator. The power cord enters the handle and is electrically connected to the proximal end of the metallic suction tube using various known connecting techniques.

The prior art electrocautery instrument described above works well when used for either suction or electrocautery. Unfortunately, two major problems arise when it is necessary to suction blood and cauterize at the same time in order to control excessive bleeding.

The first major problem arises because blood is electrically conductive. If blood reaches the surgeon's finger through the short venting passageway when the metal tube is energized, high voltage cauterizing current will pass through the blood in the passageway to the surgeon's finger. The rubber gloves typically used by the surgeon offer little protection from the high frequency, very high voltage energy and consequently a burn to the finger is likely to occur. For this reason, most manufacturers of electrocautery suction tubes caution surgeons not to use suction and cautery simultaneously.

Attempts have been made in the prior art to reduce the possibility of electrical shock. For example, U.S. Pat. No. 3,828,780 entitled COMBINED ELECTROCOAGULATOR-SUCTION INSTRUMENT issued on Aug. 13, 1974 to Charles F. Morrison, Jr., describes a suction coagulator using an exterior finger port and a passageway to the suction coagulator using an exterior finger port and a passageway to the suction cavity for controlling the suction applied to the tip of the instrument. According to the main teaching in that patent, the exterior vacuum control, finger vent hole is located upstream of the point where the venting air passageway communicates with the hollow interior cavity of the handle. The theory behind the structure described in U.S. Pat. No. 3,828,780 is that the location of the venting port with respect to the proximal end of the metallic tube and the venting air passageway prevents blood from reaching the surgeon's finger because in order to blood to reach the surgeon's finger, it must flow up the venting passageway in a direction opposite the direction of flow urged by suction. Unfortunately, independent experiments show that the theory works some of the time but a problem develops if the cannula suddenly clogs while the suction device is filled with blood and at the same time the surgeon's finger completely blocks the vent hole for maximum suction. Under such conditions, blood flow will stop and the suction vacuum will draw air out of the venting passageway causing it to fill with blood. It is apparent that the device described in U.S. Pat. No. 3,838,780 helps reduce burn hazards to surgeons but does not absolutely prevent its occurrence.

In order to demonstrate this problem in a clinical setting, a 75 pound pig was anesthetized and in incision was made to expose the viscera. Large blood vessels were located and severed to create pools of blood in the order of 2 cubic centimeters. The device described in U.S. Pat. No. 3,828,780 was used at maximum suction to suction the blood. After approximately a half cubic centimeter of blood had been drawn into the suction device, the tip of the cannula was pressed against the bleeding tissue which immediately clogged the tip. This process was repeated several times until the initial 2 cubic centimeters of blood was completely suctioned up. The procedure was repeated six times during the course of research and evidence of substantial amounts of blood in the venting passage was found after five of the six experiments. The same procedure was performed using the preferred embodiment of the present invention and there was no evidence of blood in the venting passageway after the experiments were completed.

The second major problem with regard to prior art devices such as described in U.S. Pat. No. 3,828,780 stems from the fact that a tube with an open distal end is not an efficient design for a suction device when used around tissue because the tip tends to clog easily. This occurs for several reasons. First, approximately 85% of the time conventional electrocautery devices are used to control bleeding from oozing beds such as those found after the removal of adenoids and tonsils. The suction tip of the device must be brought within several millimeters of the bleeding tissue to keep the field clear of blood in order to perform those procedures. As a result, tissue is constantly being drawn into the suction tip creating a clogging problem. That is one of the reasons for the use of a suction control finger operated vent hole such as described in U.S. Pat. No. 3,828,780. The surgeon uses the vent hole to stop suction in order to draw the suction tube away from tissue that is sucked into the suction end. This nuisance becomes magnified when the surgeon must touch tissue he is cauterizing while maintaining a field clear of blood using suction. The problem prompts many surgeons to use a Yankauer suction tube (typically metallic) alongside the cautery suction tube to guarantee suction capability during tonsillectomies. This is a dangerous practice because burns to the patient can occur if the cautery tip touches the metal Yankauer suction tube during activation. Second, during cautery procedures, tissue and coagulated blood tend to stick to the suction tip of the cannula causing it to eventually clog up. Numerous methods have been tried to prevent this, but none have been found adequate. The present invention according to its preferred embodiment provides secondary ports which when optimally located with respect to the primary port help to decrease clogging. This feature, in combination with an improved suction control, finger operated vent port arrangement helps to substantially reduce the possibility of electrical shock or burn to the surgeon.

U.S. Pat. Nos. 2,888,928; 3,595,234 and 3,610,242 were cited in the prosecution of U.S. Pat. No. 3,828,780 and are generally relevant to the state of the prior art.

SUMMARY OF THE INVENTION

Briefly described, the invention comprises a suction coagulator including an improved suction control, finger operated venting system which cooperates with an anti-clog tip. The invention serves to substantially minimize the electrical shock hazard that a surgeon may experience by reducing the possibility of electrically conductive blood backing up into the vent passageway. A nonconductive plastic handle is attached to the proximal end of an insulated, conductive metal cannula at the distal end of which is located the cauterizing suction tip. A standard suction fitting at the rear end of the handle communicates through the hollow interior cavity of the handle and the interior channel of the tube with the cauterizing tip. A suction control, finger operated venting port is located on the exterior of the handle and connected by a U-shaped passageway to the interior cavity. The suction control, finger operated venting port is axially located at least parallel with or preferably downstream from the proximal end of the metal cannula where it enters the interior cavity of the handle, thereby reducing the tendency of the passageway to fill up with blood. The cauterizing tip includes a primary suction port at the distal thereof and at least one secondary suction port located on the sidewall of the cannula and approximately 1-5 millimeters downstream from the primary port. It has been found that the improved suction control venting port structure along with the anti-clog capabilities of the secondary ports combine to substantially decrease the likelihood of a surgeon receiving electrical shocks or burns from the use of the invention.

These and other features of the invention will be more fully understood by reference to the following drawings.

BRIEF DESCRIPTION OF THE DRAWINGS

FIG. 2A is a side elevational view of the preferred embodiment.

FIG. 2B is a top plan view of the proposed embodiment.

FIG. 3 is a side cross-sectional view of the preferred embodiment.

DETAILED DESCRIPTION OF THE INVENTION

Figure 1:
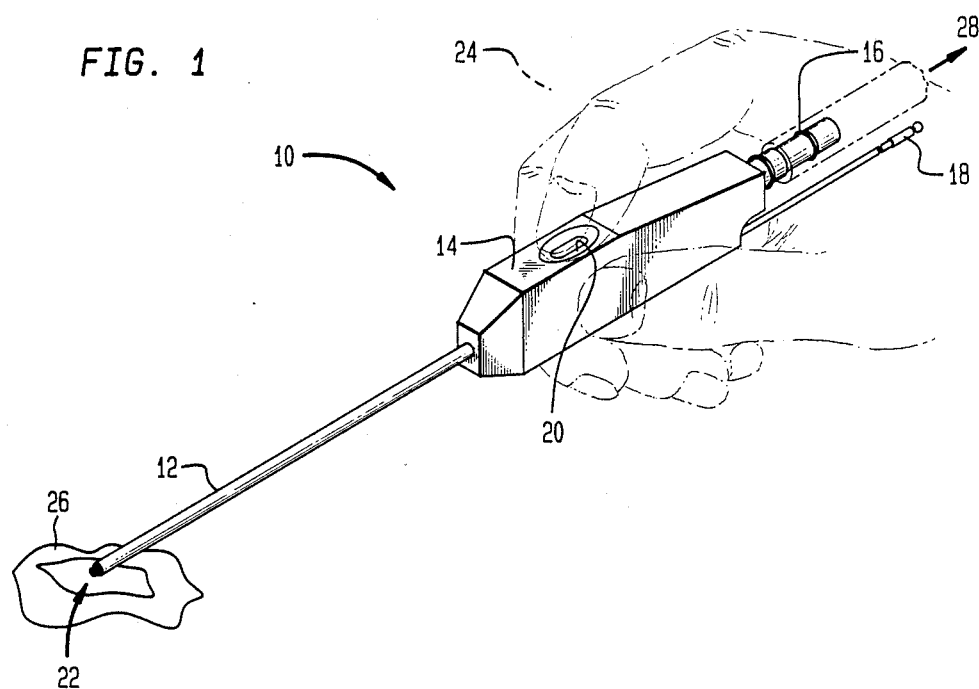
FIG. 1 is a perspective view of the preferred embodiment of the invention showing the device in the hand of a surgeon.

During the course of this description like numbers will be used to identify like elements according to the different views which illustrate the invention.

an antishock, anticlog suction coagulator 10 according to the preferred embodiment of the invention is illustrated in FIG. 1. Suction coagulator 10 includes as its major components a hollow suction tube or cannula 12, a nonconductive, plastic handle 14, a standard suction fitting 16 and an electrical cord 18 which provides power to the cauterizing tip 22 of the cannula 12. Exterior suction control, finger operated venting port 20 is used to control the suction applied to cauterizing tip 22. Typically the index finger of the surgeon's hand 24 is selectively placed over or removed from venting port 20 to control the amount of suction applied to an open wound field 26. Invention 10 is preferably employed in an environment where bleeding can be heavy, for example, during tonsillectomies or the removal of adenoids. Suction for tip 22 is provided by a conventional hose 28 which attaches to a suction coupling or fitting 16.

Figure 4:
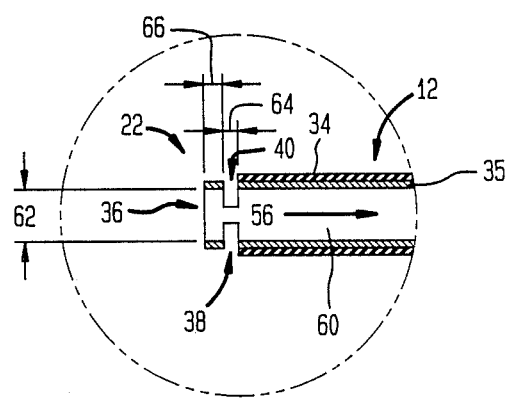
FIG. 4 is a detail side cross-sectional view of the anti-clogging tip of the preferred embodiment.

FIGS. 2A and 2B illustrate the exterior features of the preferred embodiment 10. Plastic handle 14 includes a front section 30 and a rear section 32 which fit together during assembly. Details of the cauterizing tip 22 are illustrated in FIG. 4. According to the detail of FIG. 4 an insulating sleeve 34 surrounds the metal cannula 35 collectively referred to as tube or cannula 12. A pair of secondary ports 38 and 40 are located in the sidewall of cannula 12 and approximately 1 millimeter-5 millimeters downstream of primary port 36.

For optional results, the total area of the secondary ports 38 and 40 should be approximately ⅓ of to equal to the total area of the primary port 36. Cannula 12 includes a hollow interior channel 60 having an inside diameter 62 in the range of 1 to 5 millimeters and an outside diameter in the range of 2 mm to 6 mm with a wall thickness of about 0.5 mm. Slots 38 and 40 preferably have a width 64 in the range of 0.5 mm to 2 mm with a preferable width 64 of 0.8 mm. The distance of the secondary ports 38 and 40 from the primary port 36 is in the range of 1-5 millimeters and for a 9 French cannula is preferably 1.3 mm. The suction supplied by tubing 28 to hose fitting 16 draws air in a downstream direction as shown by arrow 56 in channel 60.

The vertical side cross-sectional view of FIG. 3 illustrates in detail the structure of the interior cavity 44 in handle 14. Circular interior cavity 44 has an interior diameter of approximately 6 mm and a range of 3 mm to 7 mm. The air drawn through fitting 16 also passes in a downstream direction as illustrated by arrow 56 through interior cavity 44. Tube 12 includes a proximal or rear end 46 which is opposite from the distal or front cauterizing tip 22. The primary port 36 of the cauterizing tip 22 is connected by channel 60 to the interior cavity 44 in handle 14 and by fitting 16 to the source of suction 28. Interior cavity 44 is connected by a switchback passageway 48, having a U-shaped cross-section to the exterior suction control finger operated vent port 20. Passageway 48 has a diameter in the range of 3 mm to 5 mm and a length of approximately 12 mm. Arrows 56 and 58 respectively indicate the downstream direction of the suction air. Gasket 50 and O-ring seal 52 help to support cannula 12 and hold it in position in handle 14. A standard electrical connection, which could be solder or any other well known material is employed to electrically connect cord 18 to the metal portion of cannula 12 so that conventional high frequency electrical power is supplied to the cauterizing tip 22. Handle 14 is preferably formed from two injection molded plastic parts 30 and 32 which can be snap-fitted together after the cannula 12 is inserted in the front portion 30 and secured therein by gasket 50 and O-ring seal 52.

An important feature of the invention is the fact that the suction control, finger operated vent port 20 is located downstream of the proximal end 46 of the cannula 12. According to the preferred embodiment of the invention 10, the proximal end 46 should be axially located slightly upstream from the suction control finger vent port 20 and offset there from by distance 68 which can be in the range of 0.5 mm to 12 mm.

This means that the U-shaped venting air passage 48 connects with the main air passage 44 at a point axially upstream of the finger venting port 20 location. This is in direct contrast to the cited prior art, especially as described in U.S. Pat. No. 3,828,780 in which the venting passageway must communicate with the main air passage at a location downstream of the finger vent port.

In operation it has been found that the preferred embodiment 10 of the present invention substantially decreases the chance of receiving an electrical burn or shock as compared to prior art devices. As previously described a 75 pound pig was anesthetized and 6 experiments were performed thereon. When a prior art device such as described in U.S. Pat. No. 3,828,780 was employed, evidence of conductive blood was found in the venting passageway after five of six experiments during which the tip of the cannula was pressed against the bleeding tissue which caused it to immediately become clogged. When the same set of experiments was performed upon the preferred embodiment 10 of the present invention, no evidence of blood was found in the venting passageway.

The theory behind the improved characteristics of the present invention 10 is as follows. According to the preferred embodiment 10, the suction passage 60 runs forward to enter the interior cavity 44 at the most forward possible position. Under such circumstances, the main suction passage or cavity 44 in the handle 14 is slightly larger than the diameter of channel 60 so that the suction cannula 12 can run concentrically within the interior cavity 44 a short distance downstream. Venting air through passageway 58 within the preferred embodiment 10 flows upstream with respect to the downstream flow of air in the direction of arrow 56 and then enters the forward portion of the annular interior space 44 formed between the cannula 12 and the interior of the handle 14. This structure has been found to work exceptionally well during partial venting. Blood cannot flow up the passage 48 with the vent hole 20 completely closed for maximum suction because air trapped in the venting passage 48 prevents blood flow up the passage. The structure also prevents blood from flowing up the passage 44 if the cannula 12 becomes clogged because the degree of suction vacuum available in operating rooms is typically insufficient to draw air out of the venting passage in a direction opposite the suction direction.

It was discovered that the clogging of prior art cauterizing tips contributed to the prior art problem of having electrically conductive blood back up into the suction control passageway. The anticlog cauterizing tip 22 according to the preferred embodiment of the invention 10 tends to clog much less than prior art tips which have only a single intake port. The improved cauterizing tip 22 when combined with the unique structure of the venting passageway 48 synergistically results in a suction coagulator 10 that is virtually free of clogging and shock hazards.

It has also been found that the secondary ports 38 and 40 can be of almost any shape (e.g., circular, square, rectangular, etc.) but must be in relatively close proximity of the primary port 36 in order to be effective. A pair of slots 38 and 40 opposite each other works very well. As previously described the total area of the secondary ports 38 and 40 should be in the range of between ⅓ to equal the area of the primary port 36. Ports 38 and 40 are optimally located in the range of 1–5 millimeters for a 9 French cannula.

Bleeding control studies employing the preferred embodiment 10 using rabbit and swine livers show the following advantages of the cauterizing tip 22 over prior art cauterizing tips:

(1) The distribution of suction flow around the cauterizing tip 22 of the present invention 10 minimizes the tendency of tissue to be drawn into the primary port 36.

(2) The secondary ports 38 and 40 rarely clog up so that suction of blood through the secondary ports 38 and 40 continues even when the primary port 36 is clogged. Repeated evaluations in veterinary evaluations have shown the advantage of secondary ports to be dramatic. In side-by-side comparisons with other suction tubes, the secondary port structure continued to keep bleeding beds clear of blood even after the primary port 36 became useless after clogging. It has been found however that the secondary ports 38 and 40 must be located close enough to the cannula tip 22 so that the secondary suction field is strong enough to lift fluid, (i.e., blood) from the plane of the tip up to the secondary port location.

While the invention has been described with reference to a preferred embodiment thereof, it will be understood by those of ordinary skill in the art, that modifications can be made to the structure and elements of the invention without departing from the spirit and scope of the invention as a whole.

I claim:

1. A suction coagulator apparatus comprising:
a hollow, conductive tube having exterior side walls, a distal end, a proximal end at the opposite end of said tube from said distal end and a channel therethrough for connecting said proximal and distal ends;
a handle having a front end attached to the proximal end of said tube, a rear end having a suction fitting thereon, and an interior cavity for connecting said suction fitting to the channel in said tube such that when suction is applied to said suction fitting, air is drawn in through the distal end of said tube in a downstream direction through the channel in said tube and then through said interior cavity to said suction fitting;

electrical connection means attached to said apparatus for making electrical connection with said tube; and, vent means located in said handle for communicating between said interior cavity and the exterior of said handle, said vent means including a passageway opening onto said interior cavity at one end and onto a finger venting port at the other end on the exterior of said handle such that said finger venting port is closer to the rear end of said handle than is the point at which air drawn through said hollow, conductive tube enters said interior cavity.

wherein air drawn in through said finger venting port by said suction initially travels upstream through said passageway until it enters said interior cavity at which point it travels downstream.

2. The apparatus of claim 1 wherein the distal end of said tube comprises a coagulating tip having a primary suction port at the end thereof.

3. The apparatus of claim 2 further comprising: secondary suction port means located in the exterior sidewalls of said tube.

4. The apparatus of claim 3 wherein said secondary suction port means is located in the range of 1 mm to 5 mm from said primary suction port.

5. The apparatus of claim 4 wherein said secondary suction port means comprises at least one port in the sidewall of said tube.

6. The apparatus of claim 5 wherein said secondary suction port means comprises at least two ports having a slot-like shape and locate on opposite sides of the tube from one another.

7. The apparatus of claim 6 further comprising: an electrical insulation cover attached to and surrounding at least a portion of said tube for providing electrical insulation thereto.

8. The apparatus of claim 7 further comprising: gasket means housed on the inside of said handle for sealing the junction between said tube and said handle.

9. The apparatus of claim 8 further comprising: O-ring seal means housed on the inside of said handle for providing support to said tube.

10. The apparatus of claim 9 wherein said handle comprises at least two sections including a front section for supporting said tube and a rear section for carrying said suction fitting which are connectable together to form a unitary handle assembly.

11. The apparatus of claim 10 wherein said electrical connection means includes an electric wire receivable in said handle and electrically connectable to the conductive portion of said tube near said proximal end thereof.

12. The apparatus of claim 11 wherein said finger venting port is located between said proximal end of said tube and said rear end of said handle.

13. The apparatus of claim 12 wherein the area of said secondary port means is in the range of approximately one-third to equal to the area of the primary suction port.

14. The apparatus of claim 1 wherein said passageway has a substantially U-shaped cross section.

15. A suction coagulator apparatus comprising:
a hollow, conductive tube having exterior side walls, a distal end, a proximal end at the opposite end of said tube from said distal end and a channel therethrough for connecting said proximal and distal ends;

a handle having a front end attached to the proximal end of said tube, a rear end having a suction fitting thereon, and an interior cavity for connecting said suction fitting to the channel in said tube such that when suction is applied to said suction fitting, air is drawn in through the distal end of said tube in a downstream direction through the channel in said tube and then through said interior cavity to said suction fitting;

electrical connection means attached to said apparatus for making electrical connection with said tube; and vent means located in said handle for communicating between said interior cavity and the exterior of said handle, said vent means includijng a passageway opening onto said interior cavity at one end and onto a finger venting port at the other end on the exterior of said handle, wherein air drawn in through said finger venting port by said suction initially travels upstream through said passageway until it enters said interior cavity at which point it travels downstream.

* * * * *